(12) United States Patent
Tirtowidjojo et al.

(10) Patent No.: US 8,927,792 B2
(45) Date of Patent: Jan. 6, 2015

(54) PROCESS FOR THE PRODUCTION OF CHLORINATED AND/OR FLUORINATED PROPENES

(75) Inventors: Max M. Tirtowidjojo, Lake Jackson, TX (US); William J. Kruper, Jr., Sanford, MI (US); Kurt F. Hirsekorn, Midland, MI (US); Debashis Chakraborty, Lake Jackson, TX (US)

(73) Assignee: Dow AgroSciences, LLC, Indianapolis, IN (US)

( * ) Notice: Subject to any disclaimer, the term of this patent is extended or adjusted under 35 U.S.C. 154(b) by 0 days.

(21) Appl. No.: 13/575,266

(22) PCT Filed: May 30, 2012

(86) PCT No.: PCT/US2012/039906
§ 371 (c)(1),
(2), (4) Date: Jul. 25, 2012

(87) PCT Pub. No.: WO2012/170239
PCT Pub. Date: Dec. 13, 2012

(65) Prior Publication Data
US 2014/0088329 A1    Mar. 27, 2014

Related U.S. Application Data

(60) Provisional application No. 61/494,455, filed on Jun. 8, 2011.

(51) Int. Cl.
C07C 17/26 (2006.01)
C07C 17/38 (2006.01)
C07C 21/073 (2006.01)
C07C 17/269 (2006.01)

(52) U.S. Cl.
CPC ............ C07C 21/073 (2013.01); C07C 17/269 (2013.01); C07C 17/26 (2013.01)
USPC ........................................................ 570/237

(58) Field of Classification Search
CPC ...... C07C 17/269; C07C 21/18; C07C 17/263
See application file for complete search history.

(56) References Cited

U.S. PATENT DOCUMENTS

| | | |
|---|---|---|
| 2,119,484 A | 5/1938 | Levine |
| 2,299,441 A | 9/1939 | Vaughan |
| 2,179,378 A | 11/1939 | Metzger |
| 2,302,228 A | 11/1942 | Kharasch et al. |
| 2,370,342 A | 2/1945 | Naeher |
| 2,378,859 A | 6/1945 | Martin |
| 2,435,983 A | 12/1945 | Schmerling |
| 2,449,286 A | 9/1948 | Fairbairn |
| 2,588,867 A | 3/1952 | Morris |
| 2,630,461 A | 3/1953 | Sachsse |
| 2,688,592 A | 9/1954 | Skeeters |
| 2,762,611 A | 9/1956 | Monroe |
| 2,765,359 A | 10/1956 | Pichler |
| 2,973,393 A | 2/1961 | Monroe |
| 3,000,980 A | 9/1961 | Asadorian |
| 3,094,567 A | 6/1963 | Eaker |
| 3,444,263 A | 5/1969 | Fernald |
| 3,446,859 A | 5/1969 | Weil |
| 3,502,734 A | 3/1970 | Baird |
| 3,551,512 A | 12/1970 | Loeffler |
| 3,558,438 A | 1/1971 | Schoenbeck |
| 3,651,019 A | 3/1972 | Asscher |
| 3,676,508 A | 7/1972 | Krekeler |
| 3,819,731 A * | 6/1974 | Pitt et al. ........................ 570/187 |
| 3,823,195 A | 7/1974 | Smith |
| 3,872,664 A | 3/1975 | Lohmann |
| 3,914,167 A | 10/1975 | Ivy |
| 3,926,758 A | 12/1975 | Smith |
| 3,948,858 A | 4/1976 | Wiersum |
| 3,954,410 A | 5/1976 | Pohl |
| 4,051,182 A | 9/1977 | Pitt |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |

(Continued)

FOREIGN PATENT DOCUMENTS

| | | |
|---|---|---|
| CH | 609022 A5 | 2/1979 |
| CN | 101492341 | 7/2009 |

(Continued)

OTHER PUBLICATIONS

Shelton et al. (Journal of Organic Chemistry (1958), 23, 1876-80).*
Gault et al., "Sur la chloruatoin du chloroforme", Comptes Rendus Hebdomadaires des seances de L'Academie de Sciences, 1924, pp. 467-469, 179.
Gerding et al., "Raman Spectra of Aliphatic Chlorine Compounds II. Chloroethanes and chloropropanes", Recueil des travaux chimiques des pays bas, 1955, pp. 957-997.

(Continued)

Primary Examiner — Sudhakar Katakam
Assistant Examiner — Jennifer C Sawyer
(74) Attorney, Agent, or Firm — Carl D Corvin; KSJLAW, LLC.

(57) ABSTRACT

Processes for the production of chlorinated and/or fluorinated propenes provide good product yield with advantageous impurity profiles in the crude product. Advantageously, the processes may be conducted at lower temperatures than 600° C., or less than 500° C., so that energy savings are provided, and/or at higher pressures so that high throughputs may also be realized. The use of catalysts or initiators may provide additional enhancements to conversion rates and selectivity, as may adjustments to the molar ratio of the reactants.

22 Claims, 1 Drawing Sheet

(56) References Cited

U.S. PATENT DOCUMENTS

| | | | |
|---|---|---|---|
| 4,702,809 A | 10/1987 | Mueller | |
| 4,714,792 A | 12/1987 | Muller | |
| 4,716,255 A | 12/1987 | Muller | |
| 4,726,686 A | 2/1988 | Wolf | |
| 4,727,181 A | 2/1988 | Kruper | |
| 4,894,205 A | 1/1990 | Westerman | |
| 4,902,393 A | 2/1990 | Muller | |
| 4,999,102 A | 3/1991 | Cox | |
| 5,057,634 A | 10/1991 | Webster | |
| 5,132,473 A | 7/1992 | Furutaka | |
| 5,171,899 A | 12/1992 | Furutaka | |
| 5,254,771 A | 10/1993 | Cremer | |
| 5,254,772 A | 10/1993 | Dukat | |
| 5,254,788 A | 10/1993 | Gartside | |
| 5,262,575 A | 11/1993 | Dianis | |
| 5,315,044 A | 5/1994 | Furutaka | |
| 5,414,166 A | 5/1995 | Kim | |
| 5,684,219 A | 11/1997 | Boyce | |
| 5,689,020 A | 11/1997 | Boyce | |
| 5,811,605 A | 9/1998 | Tang | |
| 5,895,825 A | 4/1999 | Elsheikh | |
| 5,986,151 A | 11/1999 | Van Der Puy et al. | |
| 6,111,150 A | 8/2000 | Sakyu | |
| 6,118,018 A | 9/2000 | Savidakis | |
| 6,160,187 A | 12/2000 | Strickler | |
| 6,187,976 B1 | 2/2001 | Van Der Puy | |
| 6,229,057 B1 | 5/2001 | Jackson | |
| 6,472,573 B1 | 10/2002 | Yamamoto | |
| 6,538,167 B1 | 3/2003 | Brown | |
| 6,545,176 B1 | 4/2003 | Tsay | |
| 6,551,469 B1 | 4/2003 | Nair | |
| 6,610,177 B2 | 8/2003 | Tsay | |
| 6,683,216 B1 | 1/2004 | Zoeller | |
| 6,825,383 B1 | 11/2004 | Dewkar | |
| 6,958,135 B1 | 10/2005 | Filippi | |
| 7,117,934 B2 | 10/2006 | Lomax | |
| 7,189,884 B2 | 3/2007 | Mukhopadhyay | |
| 7,226,567 B1 | 6/2007 | Olbert | |
| 7,282,120 B2 | 10/2007 | Braun | |
| 7,297,814 B2 | 11/2007 | Yada | |
| 7,345,209 B2 | 3/2008 | Mukhopadhyay | |
| 7,371,904 B2 | 5/2008 | Ma | |
| 7,378,559 B2 | 5/2008 | Verwijs | |
| 7,396,965 B2 | 7/2008 | Mukhopadhyay | |
| 7,511,101 B2 | 3/2009 | Nguyen | |
| 7,521,029 B2 | 4/2009 | Guetlhuber | |
| 7,588,739 B2 | 9/2009 | Sugiyama | |
| 7,659,434 B2 | 2/2010 | Mukhopadhyay | |
| 7,674,939 B2 | 3/2010 | Mukhopadhyay | |
| 7,687,670 B2 | 3/2010 | Nappa | |
| 7,695,695 B2 | 4/2010 | Shin | |
| 7,714,177 B2 | 5/2010 | Mukhopadhyay | |
| 7,836,941 B2 | 11/2010 | Song | |
| 7,880,040 B2 | 2/2011 | Mukhopadhyay | |
| 7,951,982 B2 | 5/2011 | Mukhopadhyay | |
| 8,058,486 B2 | 11/2011 | Merkel | |
| 8,058,490 B2 | 11/2011 | Strebelle | |
| 8,071,825 B2 | 12/2011 | Johnson | |
| 8,071,826 B2 | 12/2011 | Van Der Puy | |
| 8,076,521 B2 | 12/2011 | Elsheikh | |
| 8,084,653 B2 | 12/2011 | Tung | |
| 8,115,038 B2 | 2/2012 | Wilson | |
| 8,123,398 B2 | 2/2012 | Teshima et al. | |
| 8,158,836 B2 | 4/2012 | Pigamo et al. | |
| 8,232,435 B2 | 7/2012 | Sievert | |
| 8,367,867 B2 | 2/2013 | Zardi | |
| 8,614,363 B2 | 12/2013 | Wilson | |
| 2001/0018962 A1 | 9/2001 | Joshi | |
| 2002/0110711 A1 | 8/2002 | Boneberg | |
| 2006/0150445 A1 | 7/2006 | Redding | |
| 2006/0292046 A1 | 12/2006 | Fruchey | |
| 2007/0112229 A1 | 5/2007 | Mukhopadhyay | |
| 2007/0197841 A1 | 8/2007 | Mukhopadhyay | |
| 2007/0265368 A1 | 11/2007 | Rao | |
| 2008/0021229 A1 | 1/2008 | Maughon et al. | |
| 2008/0118018 A1 | 5/2008 | Schrauwen | |
| 2008/0207962 A1 | 8/2008 | Rao | |
| 2009/0018377 A1 | 1/2009 | Boyce | |
| 2009/0030249 A1 | 1/2009 | Merkel | |
| 2009/0099396 A1 | 4/2009 | Mukhopadhyay | |
| 2009/0117014 A1 | 5/2009 | Carpenter | |
| 2009/0203945 A1 | 8/2009 | Mukhopadhyay | |
| 2009/0306438 A1 | 12/2009 | Sievert | |
| 2010/0185029 A1 | 7/2010 | Elsheikh | |
| 2010/0210883 A1 | 8/2010 | Mukhopadhyay | |
| 2011/0083955 A1 | 4/2011 | Tirtowidjojo et al. | |
| 2011/0172472 A1 | 7/2011 | Sakyu | |
| 2011/0178343 A1 | 7/2011 | Kruper | |
| 2011/0218369 A1 | 9/2011 | Elsheikh | |
| 2011/0251425 A1 | 10/2011 | Penzel | |
| 2011/0251442 A1 | 10/2011 | Okamoto | |
| 2012/0035402 A1 | 2/2012 | Wilson | |
| 2012/0041239 A1 | 2/2012 | Suzuki | |
| 2012/0065434 A1 | 3/2012 | Nose | |
| 2014/0081055 A1 | 3/2014 | Tirtowidjojo | |

FOREIGN PATENT DOCUMENTS

| | | |
|---|---|---|
| CN | 101544535 | 9/2009 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 A | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 453818 | 10/1991 |
| EP | 1018366 | 12/2000 |
| FR | 1546709 | 11/1968 |
| GB | 471188 | 8/1937 |
| GB | 857086 | 12/1960 |
| GB | 1134585 | 11/1968 |
| GB | 1381619 | 1/1975 |
| JP | 54-079207 A | 6/1979 |
| JP | 2001151708 | 6/2001 |
| JP | 2001213820 | 8/2001 |
| JP | 2007021396 | 2/2007 |
| JP | 2008063314 | 3/2008 |
| JP | 2009046653 | 3/2009 |
| JP | 2011144148 | 7/2011 |
| LU | 52247 | 12/1966 |
| RU | 899523 | 1/1982 |
| WO | 0138271 | 5/2001 |
| WO | 0138275 | 5/2001 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 6/2012 |
| WO | 2012166393 | 12/2012 |

OTHER PUBLICATIONS

Hatch et al., "Allylic Chlorides. XV. Preparation and Properties of the 1,2,3-Trichlooropropenes", JACS, Jan. 5, 1952, pp. 123-126, 74(1).
Hatch et al., "Allylic Chlorides. XVIII. Preparation and Properties of 1,1,3-Tricloro-2fluoro-1-propene and 1,1,2,3-Tetrachloro-1-propene", JACS, Jul. 5, 1952, pp. 3328-3330, 74(13).
Leitch, "Organic Deuterium Compounds: V. The Chlorination of Propyne and Propyne-d4", Canadian Journal of Chemistry, Apr. 1, 1953, pp. 385-386, 31(4).
Levanova et al., "Thermocatalytic Reactions of Bromochloropropanes", Russian Journal of Physical Chemistry, Chemical Society, London, GB, Jan. 1, 1983, pp. 1142-1146 vol. 57.

(56) References Cited

OTHER PUBLICATIONS

Pozdnev et al., "Chlorination of Chloroform and the conversion of methylene chloride manufacture still residues", Khim. Khim. Tekhnol., 1970, pp. 70-74, 70(4).

Skell et al., "Selectivities of pi and sigma Succinimidyl Radicals in Substitution and Addition Reactions. Appendix: Response to Walling, El-Taliawi and Zhao", JACS, 1983, pp. 5125-5131, 105(1).

Skell et al., "Reactions of BrCl with Alkyl Radicals", Tetrahedron Letters, 1986, pp. 5181-5184, 27(43).

Urry et al., Free-Radical Reactions of Diazomethanewith Reactive Bromopolychloroakanes, JACS, May 5, 1964, pp. 1815-1819, 86(9).

Wang, "Elimination Reactions of Polyhalopropanes under Emulsion Catalytic Conditions to give Halopropenes", Synthesis, Georg Thieme Verlag, Stuttgart, DE, Jan. 1, 1982, pp. 494-496, 1982(6).

Herzfelder, "Substitution in the Aliphatic Series", Berichte der Deutschen Chemischen Gesellschaft, 1893, 1257-1261, 26(11).

McBee et al., "Utilization of Polychloropropanes and Hexachloroethane", Industrial and Engineering Chemistry, Feb. 1941, 176-181, 33(2).

Mouneyrat, "Effect of chlorine on propyl chloride in the presence of anhydrous aluminum chloride", Bulletin de la Societe Chimique de Paris, Jan. 1899, 616-623, 3(21).

PCT/US12/39906, Search Report, mailed Aug. 17, 2012.

Bai et al., "Isomerization of tetrachloropropene to promote utilization ratio of triallate raw materials" Petrochemical Technology & Application, 2007, 25(1).

Boualy et al., "Kharasch Addition of Tetrachloromethane to Alkenes Catalyzed by Metal Acetylacetonates", Catalysis Communications, 2011, 1295-1297, 12.

Chai et al., "Study of Preparation of 1,1,13-Tetrachloropane", Zhejiang Chemical Industry, 2010, 1-3, 41.

Cristiano et al., "Tetraalkylphosphonium Trihalides, Room Temperature Ionic Liquids as Halogenation Reagents", J. Org. Chem., 2009, 9027-9033, 74.

Evstigneev et al., "Initiated Chlorination of Tetrachloropropane", The Soviet Chemical Industry, 1984, 835-837, 16.

Ivanov et al., "Metal phthalocyanine-catalyzed addition of polychlorine-containing organic compounds to C=C bonds", Russian Chemical Bulletin, 2009, 2393-2396, 58.

Kang et al., "Kinetics of Synthesis of 1,1,1,3,3-pentachlorobutane catalyzed by Fe-FeCl3," Chemical Research and Application, 2011, 657-660, 23.

Kharasch et al., "Chlorinations with Sulfuryl Chloride. I. The Peroxide-Catalyzed Chlorination of Hydrocarbons", 1939, 2142-2150, 61.

Khusnutdinov et al., "Addition of CCl4 to olefins catalyzed by complexes of chromium and ruthenium. Effect of Water as a Nucleophilic Additive.", Neftekhimiya, 2009, 349-356, 49(4).

Kruper et al., "Synthesis of alpha-Halocinnamate Esters via Solvolytic Rearrangement of Trichloroallyl Alcohols", J. Org. Chem., 1991, 3323-3329, 56.

Liu et al., "Process in the Synthesis of 1,1,1,3-Tetrachloropane", Guangzhou Chemicals, 2011, 41-58, 39(5).

Munoz-Molina et al., "An efficient, Selective, and Reducing Agent-Free Copper catalyst for the atom-transfer radical addition of halo compounds to activated olefins", Inorg. Chem., 2010, 642-645, 49.

Nair et al., "Atom Transfer radical addition (ATRA) of carbon tetrachloride and chlrinated esters to various olefins catalyzed by CpRu(PPh3)(PR3)Cl Complexes", Inorganica Chimica Acta, 2012, 96-103, 380.

Nishikin et al., "Reactions of methanol and ethanol with tetrachloroethylene", N.D. Zelinskii Institute of Organic Chemistry, Academy of Sciences of the USSR, Translated from Izvestiya Akademii Nauk SSSR, Seriya Khimicheskaya, 1966, 2188-2192, 12.

Rotshtein et al., "Isomer distribution on chlorination of chloropropane", Zhurnal Organicheskoi Khimii, 1966, 1539-1542, 2(9).

Semenov, "Selectivity of photochemical chlorination of chloromethane in the liquid phase", Prikladnei Khimii, 1985, 840-845, 58(4).

Tanuma et al., Partially Fluorinated metal oxide catalysts for a Friedel-Crafts-type reaction of dichlorofluoromethane with tetrafluoroethylene, Catal. Lett., 2010, 77-82, 126.

Zhao et al., "Research Progress on preparation technology of 1,1,2,3-tetrachloropropene", Zhejiang Chemical Industry, 2010, 8-11, 41(8).

Zheng et al., "Review of the Preparation of the low GWP Alternative 1,3,3,3-Tetranuoropropene", Zhejiang Chemical Industry, 2010, 5-8, 41(3).

Galitzenstein et al., "The Dehydrochlorination of Propylene Dichloride", Journal of the Society of Chemical Industry, 1950, pp. 298-304, vol. 69.

\* cited by examiner

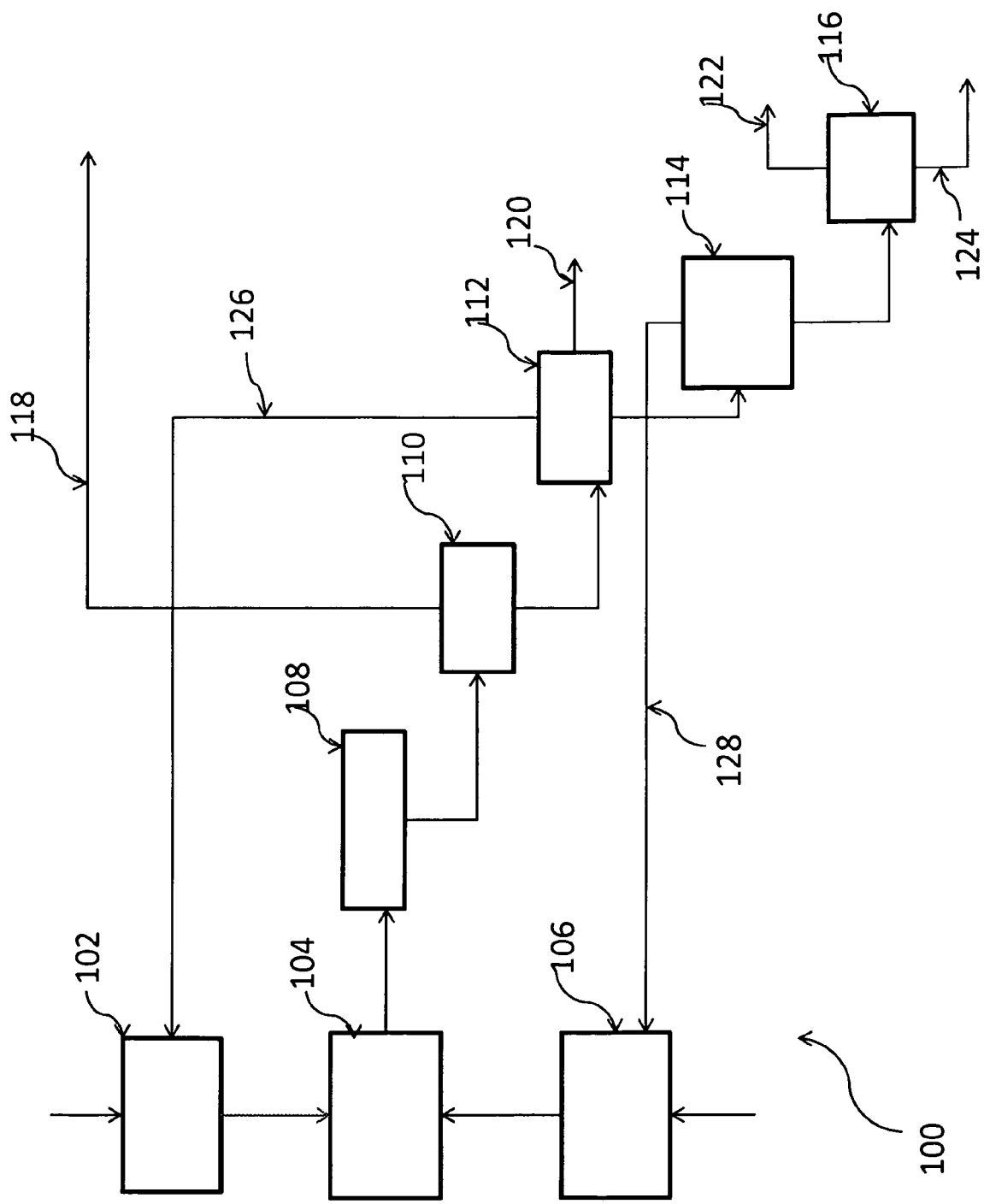

PROCESS FOR THE PRODUCTION OF CHLORINATED AND/OR FLUORINATED PROPENES

FIELD

The present invention relates to processes for the production of chlorinated and/or fluorinated propenes.

BACKGROUND

Chlorinated and/or fluorinated propenes are known to be useful as monomers in the manufacture of plastics and resins and also find use as chemical intermediates in the manufacture of, e.g., hydrofluoroolefins. Many such compounds are also known to be useful as nematocides and insecticides, and in fact, this may be their predominant use.

The commercial availability of these compounds may be undesirably limited by the processes typically utilized in their manufacture. For example, chlorinated and/or fluorinated propanes have been reacted with oxygen and in the presence of a catalyst and at high temperatures to produce chlorinated propenes. Desired chlorinated and/or fluorinated propenes have also been obtained by dehydrochlorinating trichloropropenes in the presence of oxygen or by reacting dichloropropenes with chlorine and/or allyl chloride and/or chloropropenes to provide the desired chlorinated propene. However, all of these processes are complicated multi-step processes, and many require the use of catalysts and thus, the removal of one or more catalysts from the product.

The process most commonly relied upon for the production of one exemplary chlorinated propene, 1,3-dichloropropene, is actually a process for the production of allyl chlorides. In such processes, the thermal chlorination of propene provides about 70-85% selectivity to allyl chloride and 15-30% dichlorinated byproducts. Up to about 50% of the byproducts, in turn, may typically comprise about 50% 1,3-dichloropropene, with the remainder consisting of other chlorinated propenes, 1,2-dichloropropane, six carbon olefins and other chlorinated six carbon compounds.

Although this process accounts for a large majority of the production of 1,3-dichloropropene, it is suboptimal at least because it links the production of 1,3-dichloropropene to the production rate and demand for allyl chloride. The conventional process can also be found lacking when the end product is desirably a single isomer rather than a racemic mixture. The cis isomer of 1,3-dichloropropene is known, for example, to be about twice as active as a nematocide as the trans isomer. However, while the cis isomer is slightly more volatile than the trans isomer, and therefore should be separable by fractional distillation, it has been found that both this distillation and any subsequent isomerization of the trans isomer are greatly impeded by the presence of a small proportion of six carbon olefins that boil very close to the boiling temperature of the dichlorinated propene fraction.

Although simplified, one-step processes have been developed for the manufacture of chlorinated and/or fluorinated propenes, these processes can have limited commercial applicability due to their limited throughput. Whether multi-step or one-step, many of the conventional manufacturing processes for the production of chlorinated and/or fluorinated propenes may typically result in the formation of large quantities of reaction by-products that must then be separated from the product and disposed of, typically at great expense, further limiting their commercial potential.

It would thus be desirable to provide improved processes for the production of chlorinated and/or fluorinated propenes. More particularly, such processes would provide an improvement over the current state of the art if they could by decoupled from the manufacture of products in which they are produced as by-products, or as a portion of a mixture of by-products from which their separation is difficult. Cost savings and/or improvements in reaction selectivity would also provide commercial advantage and be appreciated by the art.

BRIEF DESCRIPTION

The present invention provides efficient processes for the production of chlorinated and/or fluorinated propenes. Advantageously, the processes are one-step processes, thereby providing significant time, operating and capital cost savings over conventional multi-step processes for the production of chlorinated propenes. Further, the present processes provide a reaction mixture from which the chlorinated and/or fluorinated propene(s) are more easily separated and/or purified to provide the desired end product than conventional processes, and so, additional cost savings can be seen.

More specifically, the processes comprise reacting a dichloroethylene or a chlorofluoroethylene with a methane, chloromethane, fluoromethane, or chlorofluoromethane to provide the chlorinated or fluorinated propene. The dichloroethylene or chlorofluoroethylene has the formula CHCl=CHX, where X is Cl or F, while the methane, chloromethane, fluoromethane or chlorofluoromethane may desirably have the formula $CH_{(4-a)}X_a$, wherein a is 0-3. The chlorinated or fluorinated propene may, in some embodiments, have the formula CHX=CH—$CH_{(3-a)}X_a$ wherein a is 0-3.

In one embodiment, the dichloroethylene or chlorofluoroethylene comprises cis/trans-1,2-dichloroethylene and the methane, chloromethane, fluoromethane or chlorofluoromethane comprises methyl chloride. In such embodiments, as well as others, the chlorinated and/or fluorinated propene may desirably comprise cis/trans 1,3-dichloropropene.

The present process provides a crude product more easily refined than that of conventional processes. That is, while one conventional process for the production of cis-1,3-dichloropropene, the production of allyl chloride, produces cis-1,3-dichloropropene as a by-product in a mixture further comprising chlorinated propenes, 1,2-dichloropropane, six carbon olefins and other chlorinated six carbon compounds, the present process provide a crude product comprising cis/trans-1,3-dichloropropene as well as the principal by-products trichloropentadiene and trichloroheptadiene. As a result, the desired dichloropropene can be separated using chlorination and/or a simple distillation.

Desirably, the processes will be conducted at ambient pressures or greater, or at a pressure of least 200 psig, or at least 250 psig. The temperature of the processes may, advantageously be lower than those utilized in conventional processes, i.e., the temperature may be less than 600° C., or less than 500° C., or less than 400° C. In some embodiments, diluents may be utilized to reduce the temperature within the reactor and, if the same is desired, may be chosen from an inert diluents, $CH_{(4-a)}X_a$, HCl, or combinations of these.

Catalysts may be utilized in the process, and in those embodiments where the same is desired, free radical initiators, such as those comprising chlorine, e.g., carbon tetrachloride, hexachloroethane, benzotrichloride, hexachloroacetone, chlorine, or combinations of these, may be utilized. The ratio of $CH_{(4-a)}X_a$ to CHCl=CHX may advantageously be greater than 1.0. Combinations of one or more of elevated pressure, lower temperatures, the use of a catalyst, and the ratio of $CH_{(4-a)}X_a$ to $CHCl=CHX$ may be utilized to provide further enhancements to the conversion rate, selectivity and/or cost savings provided by the process.

DESCRIPTION OF THE DRAWINGS

FIG. 1 shows a schematic diagram of a process according to one embodiment.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Further, "M1" may be used as an abbreviation for methyl chloride, "M2" may be used as an abbreviation for methylene chloride, "M3" may be used as an abbreviation for chloroform, and "M4" may be used as an abbreviation for carbon tetrachloride. Similarly, "DCE" may be used as an abbreviation for 1,2-dichloroethylene, "DCP" may be used, as an abbreviation for 1,3-dichloropropene, "DCHDE" can be used as an abbreviation for dichlorohexadiene, "TCPDE" can be used as an abbreviation for trichloropentadiene and "TCHTE" can be used as an abbreviation for trichloroheptatriene.

Throughout the specification, the formula $CHCl=CHX$ wherein X is Cl or F indicates the chloroethylene or chlorofluoroethylene, as the case may be, while the formula $CH_{(4-a)}X_a$, wherein a is 0-3 and each X is independently Cl or F may be used to indicate the methane, chloromethane, fluoromethane or chlorofluoromethane. Finally, the formula $CHX=CH—CH_{(3-a)}X_a$ wherein a is 0-3 and each X is independently Cl or F respectively, indicates the chlorinated and/or fluorinated propene(s).

The present invention provides efficient processes for the production of chlorinated and/or fluorinated propenes. The present processes comprise only one step, the reaction of a dichloroethylene or a chlorofluoroethylene with a methane, chloromethane, fluoromethane, or chlorofluoromethane, thus, providing a significant time and materials savings as compared to conventional processes. Additionally, the present processes may be carried out at lower temperatures than conventional processes, thus providing a cost savings, while yet also providing commercially acceptable throughputs not achieved by conventional high temperature processes.

Further, the present processes provide this good product yield while also providing low, e.g., less than 20%, or even less than 10% yield of residues/by-products. The use of catalysts may provide further enhancements e.g., to conversion rates and selectivity as may the optimization of the molar ratio of the reactants.

In additional embodiments, one or more reaction conditions of the one step process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Because of such improvements, the one-step process of the present invention may provide conversion rates of the methane, chloromethane, fluoromethane or chlorofluoromethane of at least 2%, or 5%, or 10%, or up to 15%, or in some instances, even up to 20% or greater, without substantially reducing selectivity to the chlorinated and/or fluorinated propene. Conversion rates of dichloroethylene or chlorofluoroethylene of at least 5%, or at least 10%, or at least 15%, or even up to 20% or better can be seen. Concentrations of impurities, such as redox impurities, of less than 5 mole percent, less than 2 mole percent, and in some embodiments, even less than 0.5 mole percent may also be provided. The present processes also surprisingly provide selectivities to the chlorinated and/or fluorinated propene of at least 50%, or up to 60%, up to 70%, up to 80% when chloroethylene or chlorofluoroethylene conversion is 30% or less, or up to 95% when chloroethylene or chlorofluoroethylene conversion is 20% or less.

The dichloroethylene or chlorofluoroethylene utilized in the present processes desirably have the formula $CHCl=CHX$ wherein X is Cl or F. Suitable dichloroethylenes or chlorofluoroethylenes comprise at least two hydrogen atoms. Exemplary dichloroethylenes and chlorofluoroethylenes that may be utilized in the present process thus include cis/trans-dichloroethylene and cis/trans-1-dichloro-2-fluoroethylene, or combinations of these.

The methane, chloromethane, fluoromethane or chlorofluoromethane utilized in the present processes desirably have the formula $CH_{(4-a)}X_a$, wherein a is 0-3 and each X is independently Cl or F. Suitable chloromethanes, fluoromethanes and chlorofluoromethanes comprise at least one hydrogen atom. Thus, suitable methanes, chloromethanes, fluoromethanes and chloromethanes include methane, methyl fluoride, methyl chloride, methylene fluoride, methylene chloride, methyl difluoride, methyl trifluoride, chloromethane, dichloromethane, trichloromethane, fluoromethane, difluoromethane, trifluoromethane, chloroform, chlorodifluoromethane, dichlorofluoromethane, chlorofluoromethane, or combinations of these.

The present processes may advantageously be utilized to produce chlorinated and/or fluorinated propenes in one step. In some embodiments, the chlorinated and/or fluorinated propenes that can be produced according to the present process include those having the formula $CHX=CH-CH_{(3-a)}X_a$ wherein a is 0-3. Examples of these include, for example, cis/trans-1-chloropropenes, cis/trans-1-fluoropropenes, cis/trans-1,3-dichloropropenes, cis/trans-1-chloro,3-fluoropropenes, cis/trans-3-chloro,1-fluoropropenes, cis/trans-1,3-difluoropropenes, cis/trans-1,3,3-trichloropropenes, cis/trans-1,3-dichloro,3-fluoropropenes, cis/trans-1-chloro,3,3-difluoropropenes, cis/trans-3,3-dichloro,1-fluoropropenes, cis/trans-,3-chloro,1,3-difluoropropenes, cis/trans-1,3,3,3-tetrafluoropropenes, cis/trans-1,3,3-dichloro,3-fluoropropenes, cis/trans-1,3-dichloro,3,3-difluoropropenes, cis/trans-1-chloro,3,3,3-trifluoropropenes, cis/trans-3,3,3-trichloro,1-fluoropropenes, cis/trans-3,3-dichloro,1,3-difluoropropenes, cis/trans-3-chloro,1,3,3-trifluoropropenes, cis/trans-1,3,3,3-tetrafluoropropenes.

For example, in some embodiments wherein the chloroethylene comprises cis/trans-dichloroethylene, the methane, chloromethane, fluoromethane or chlorofluoromethane, may comprise methyl chloride, methylene chloride, chloroform, methane, methyl fluoride, methyl difluoride, methyl trifluoride, chlorofluoromethane, chlorodifluoromethane, and/or dichlorofluoromethane and the chlorinated and/or fluorinated propene may comprise cis/trans-1,3-dichloropropenes, cis/trans-1,3,3-trichloropropenes, cis/trans-1,3,3,3-tetrachloropropenes, cis/trans-chloropropenes, cis/trans-1-chloro,3-fluoropropenes, cis/trans-1-chloro,3,3-difluoropropenes, cis/trans-1-chloro-3,3,3-trifluoropropenes, cis/trans-1,3-dichloro,3-fluoropropenes, cis/trans-1,3-dichloro,3,3-difluoropropenes and/or cis/trans-1,3,3-trichloro,3-fluoropropenes, respectively.

In other embodiments wherein the dichloroethylene or chlorofluoroethylene comprises 1-chloro-2-fluoroethylene, the methane, chloromethane, fluoromethane or chlorofluoromethane, may comprise methane, chloromethane, dichloromethane, trichloromethane, fluoromethane, difluoromethane, trifluoromethane, chlorofluoromethane, dichlorofluoromethane, and/or chlorodifluoromethane and the chlorinated and/or fluorinated propene may comprise cis/trans-1-fluoropropenes, cis/trans-3-chloro,1-fluoropropenes, cis/trans-3,3-dichloro,1-fluoropropenes, cis/trans-3,3,3-trichloro,1-fluoropropenes, cis/trans-1,3-difluoropropenes, cis/trans-1,3,3-trifluoropropenes, cis/trans-1,3,3,3-tetrafluoropropenes, cis/trans-3-chloro,1,3-difluoropropenes, cis/trans-3,3-dichloro,1-fluoropropenes, and/or cis/trans-3-chloro,1,3,3-trifluoropropenes, respectively.

Reaction conditions of the one-step process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to temperature, pressure, flow rates, molar ratios of reactants, use of catalysts or initiators, etc.

In one embodiment, reaction pressure is advantageously optimized, and may provide enhanced chlorinated and/or fluorinated propene selectivities, than those carried out at ambient or lower pressures. More specifically, improvements to at least the chlorinated and/or fluorinated propene selectivity are expected at pressures of greater than 0 psig, or greater than 20 psig, or greater than 35 psig, with improvement expected to increase with increase of pressure, up to 200 psig, or up to 300 psig, or up to 400 psig, or even up to 500 psig and greater. Optimizing at least pressure of the reaction in this fashion is estimated to provide chlorinated and/or fluorinated propene selectivity of at least 60%, or up to 70%, or up to 80%, or, in some embodiments, up to 95%. In other embodiments, the present processes may be carried out at ambient pressure.

The temperature of the reaction may also be optimized, and surprising results are expected when lowering the temperature, in particular when done in combination with pressure optimization. That is, although conventional processes typically call for temperatures of at least 550° C., the present process may be carried out at less than 600° C., or less than 500° C., or less than 450° C., or less than 400° C., while yet providing improvements to reactant conversions, product selectivity and lowering the capital cost associated with the use of the reactor.

The molar ratio of the reactants may also be optimized. While a 1:1 ratio of $CF_{4-a)}X_a$ to $CHCl=CHX$ or lower ratio may be used, provision of a stoichiometric excess of $CH_{(4-a)}X_a$ may provide enhancements to the present process. More particularly, any molar ratio of $CH_{(4-a)}X_a/CHCl=CHX$ in which $CH_{(4-a)}X_a$ is present in excess may be utilized and is expected to result in enhancements to the process, whether in the form of increases to conversion or selectivity, or decreases in the production of impurities. Molar ratios of greater than 1:1, or greater than 1.5, or greater than 2, or even greater than 3:1, may provide at least incremental improvements to the selectivity to the desired products. As with enhancements to temperature, any adjustments to the molar ratio may provide synergistic effects, but at least combinatorial enhancements, when utilized in conjunction with increases in reaction pressure.

Catalysts or initiators may also be utilized to enhance the present process. Surprisingly, the utilization of the same, in particular in conjunction with any of the other condition optimizations, does not result in an increase in the production of redox impurities by the process, but does provide selectivities to the chlorinated and/or fluorinated propene of at least 60%, or up to 70%, or up to 80%, or, in some embodiments, up to 90% or even higher.

Any catalyst or initiator capable of at least marginally enhancing the selectivity of the inventive process for the chlorinated and/or fluorinated propene may be utilized by itself or in a combination with others. Catalysts/initiators capable of doing so are believed to include those that are capable of removing hydrogen from methane, chloromethanes, fluoromethanes or chlorofluoromethanes to produce the corresponding radical. For example, in the case of methyl chloride, the catalyst/initiators are capable of removing hydrogen from methyl chloride to form a chloromethyl radical, e.g., $*CH_2Cl$. Such free radical initiators are well known to those skilled in the art and have been reviewed, e.g., in "Aspects of some initiation and propagation processes," Bamford, Clement H. Univ. Liverpool, Liverpool, UK., Pure and Applied Chemistry, (1967), 15(3-4), 333-48 and Sheppard, C. S.; Mageli, 0. L. "Peroxides and peroxy compounds, organic," Kirk-Othmer Encycl. Chem. Technol., 3rd Ed. (1982), 17, 27-90.

Such catalysts may typically comprise one or more chlorine or peroxide groups and/or exhibit reactor phase mobility/activity. As used herein, the phrase "reactor phase mobility/activity" means that a substantial amount of the catalyst or initiator is available for generating free radicals of sufficient energy which can initiate and propagate effective turnover of the product, chlorinated and/or fluorinated propene, within the design limitations of the reactor.

In general, the catalyst/initiator should have sufficient homolytic dissociation energies such that the theoretical maximum of free radicals is generated from a given initiator under the temperature/residence time of the process. It is especially useful to use free radical initiators at concentrations where free radical chlorination of incipient radicals is prevented due to low concentration or reactivity. Diperoxides offer an advantage of not being able to propagate competitive processes (e.g., the free radical chlorination of methylene chloride to chloroform and carbon tetrachloride).

Examples of suitable catalysts/initiators comprising chlorine include, but are not limited to carbon tetrachloride, hexachloroacetone, chlorine, chloroform, hexachloroethane, phosgene, thionyl chloride, sulfuryl chloride, trichloromethylbenzene, those comprising perchlorinated alkylaryl functional groups, or organic and inorganic hypochlorites, including hypochlorous acid, and t-butylhypochlorite, methylhypochlorite, chlorinated amines (chloramine) and chlorinated amides or sulfonamides such as chloroamine-T®, and the like. Combinations of any of these may also be utilized.

Carbon tetrachloride ($CCl_4$) and chlorine gas ($Cl_2$) are but two examples of catalyst/initiators that are readily commercially available and easily integrated into the present process, and their use can be preferred in embodiments wherein the use of a catalyst or initiator is desired.

Examples of suitable catalysts/initiators comprising one or more peroxide groups include hydrogen peroxide, hypochlorous acid, aliphatic and aromatic peroxides or hydroperoxides, including di-t-butyl peroxide, benzoyl peroxide, cumyl peroxide and the like.

In addition bis-azo initiators may have utility in effecting the addition of $CH_{(4-a)}X_a$ to $CHCl=CHX$ under the conditions of this invention.

Whatever the desired catalyst or initiator, those of ordinary skill in the art are well aware of methods of determining the appropriate concentration and method of introduction thereof. For example, many catalysts/initiators are typically introduced into the reactor zone as a separate feed, or in solution with other reactants, e.g., $CHCl=CHX$, which can be evaporated prior to the reaction zone. Also, initiators with a low boiling point can be introduced with inert gaseous diluents such as $N_2$.

The amount of any catalyst or initiator utilized will depend upon the particular catalyst/initiator chosen as well as the other reaction conditions. Generally speaking, in those embodiments of the invention wherein the utilization of a catalyst/initiator is desired, enough of the catalyst/initiator should be utilized to provide some improvement to reaction process conditions (e.g., a reduction in required temperature) or realized products, but yet not be more than will provide any additional benefit, if only for reasons of economic practicality. For purposes of illustration only, then, it is expected in those embodiments wherein a catalyst or initiator comprising carbon tetrachloride is desirably utilized, that useful concentrations thereof will range from 5 ppm to 200000 ppm, or from 10 ppm to 100000 ppm, or from 20 ppm to 50000 ppm, inclusive of all subranges therebetween.

The process can be further enhanced by subjecting the process or reactor zone to pulse laser or continuous UV/visible light sources at a wavelength suitable for inducing photolysis of the radical catalyst/initiator, as taught by Breslow, R. in *Organic Reaction, Mechanisms* W.A. Benjamin Pub, New York p 223-224. Wavelengths from 300 nm to 700 nm of the light source are sufficient to dissociate commercially available radical initiators. Such light sources include, e.g, Hanovia UV discharge lamps, sunlamps or even pulsed laser beams of appropriate wavelength or energy which are configured to irradiate the reactor chamber. Alternatively, chloromethyl radicals may be generated from microwave discharge into a bromochloromethane feedsource introduced to the reactor as taught by Bailleux et al., in Journal of Molecular Spectroscopy, 2005, vol. 229, pp. 140-144.

As mentioned above, the present invention provides economical processes for the production of chlorinated and/or fluorinated propenes, i.e., wherein one or more of the reaction conditions are optimized. In certain preferred embodiments, an initiator may be utilized in conjunction with a lower temperature and increased pressure to provide a process that results in a product stream with lower amounts of impurities. For example, the use of carbon tetrachloride as an initiator at amounts as low as 6%, is expected to provide dichloroethylene conversions of greater than 15% at temperatures of 420° C. and pressures of 260 psig.

By running at temperatures lower than 600° C., or less than 500° C. not only are process cost savings provided, but lower capital costs are associated with the use of the reactor. And yet, in these embodiments of the invention, $CHCl=CHX$ conversions of at least 5%, or at least 10%, or at least 15%, or even up to 20% or even greater can be seen, along with $CH_{(4-a)}X_a$ conversions of at least 2%, or 5%, or 10%, or up to 20%, or in some instances, even up to 40% or greater and chlorinated and/or fluorinated propene selectivities of at least 50%, or up to 60%, up to 70%, or up to 80% when $CHCl=CHX$ conversion is 30% or less, or even up to 95% when $CHCl=CHX$ conversion is 20% or less.

Surprisingly, the gas phase conditions described herein for the production of chlorinated and/or fluorinated propenes from the reaction of methane, chloromethanes, fluoromethanes or chlorofluoromethanes having the formula $CH_{(4-a)}X_a$ wherein a is from 0-3 and chloroethylene or chlorofluoroethylenes having the formula $CHCl=CHX$ wherein X is Cl or F show a preferred regioselectivity for the cis-1,3-dichloropropene to the corresponding trans by 10% or the molar ratio of cis/trans of 1.1.

The present process may be conducted in any suitable reactor. Desirably, the reactor utilized will be one wherein the reaction conditions are readily and easily altered as desired, and also, that can function without damage or fouling at the selected conditions. These are expected to include near-isothermal shells and multitube reactors where the desired temperature can be achieved by means of utilization of a heat transfer field.

Adiabatic cylindrical or tube reactors may also be used, and if used can have any desired length to diameter aspect ratio so long as preheating to the desired reaction temperature is possible. If an adiabatic reactor is utilized, a larger $CH_{(4-a)}X_a$/$CHCl=CHX$ ratio, e.g., 1.3 or greater, or a suitable diluents, such as inert diluents or $CH_{(4-a)}X_a$, may be used in order to limit the adiabatic temperature rise, i.e., to an increase in temperature of less than 50° C., preferably an increase in temperature of only from 10° C. to 20° C. Alternatively, a series of adiabatic reactors with at least one intercooler operatively disposed relative thereto can also be employed to obtain the desired overall conversion while maintaining the desired temperature rise within each reactor.

One embodiment of the process provided is shown in FIG. 1. More particularly, as shown in FIG. 1, process 100 makes use of evaporators 102 and 106, reactor 104, quench drum 108, and separation columns 110, 112, 114 and 116. During operation of process 100, the methane, chloromethane, fluoromethanes or chlorofluoromethane is evaporated and/or heated in evaporator 102, while the dichloroethylene or chlorofluoroethylenes and any desired catalyst/initiator is evaporated and, or heated in evaporator 106. After vaporizing the reactants and initiator and preheating them to the desired temperature, the reactants are fed into reactor 104 to achieve a desired conversion and selectivity to DCP.

The reaction mixture is then quenched in quench drum 108 to stop the reaction and to obtain a product. The crude product is then fed to first separation column 110 to recover anhydrous HCl in overhead stream 118. The bottom stream of first separation column 110 is then fed to a second separation column 112 to purify unreacted $CH_{(4-a)}X_a$ in overhead stream 126. Overhead stream 126 is then recycled to reactor 104 after being mixed with fresh make-up $CH_{(4-a)}X_a$ in evaporator 102.

Mid boiler byproducts, i.e., byproducts with boiling points between $CH_{(4-a)}X_a$ and CHCl=CHX, can be purged by either side draw 120 from second separation column 112 or as a purge from overhead stream 126. The bottom stream of second separation column 112 is then fed to third separation column 114, where unreacted CHCl=CHX is drawn overhead via line 128 to be recycled to reactor 104 after being mixed with fresh CHCl=CHX feed in evaporator 106. Alternatively, mid boiler byproducts can also be purged from overhead line 128.

The crude DCP coming out of the bottom of third separation column 114 is further purified from heavier byproducts as overhead stream 122 in last separation column 116. Alternatively, before feeding the DCP crude to separation column 116, some of the identified heavy byproducts in the crude such as chlorinated pentadiene and hepatriene could also be further chlorinated to further improve the purity of the DCP in final column overhead 122.

EXAMPLE 1

Materials. Methyl chloride (M1) was purchased from Airgas. Hexachloroacetone (HCA) and carbon tetrachloride (M4) were used as received from Aldrich. 1,2-Dichloroethylene (DCE) was purchased from Aldrich (98% purity) as a mixture of isomers (85% trans, 15% cis) and stored under nitrogen at all times. 1,3-Dichloropropene (DCP) was purchased from Aldrich (98% purity) as a mixture of isomers (53% cis, 47% trans).

A reactor having a reactor tube with an 0.75 inch O.D. is constructed of Hastelloy-C material to enable high temperatures (>450° C.) and pressures (400 psig) in addition to its resistance to corrosion by HCl. The exterior wall of the reaction zone (10 inch long, 49.5 cc volume) is heated by band heaters controlled by thermocouples. The reactant gases, at mixture ratio of M1/DCE of 1 to 4, are used at temperatures from 350° C. to 420° C. and pressure of from 260 to 400 psig and are mixed and preheated prior to entering the reaction zone, which is at a temperature of from 230° C. to 240° C.

Below the reaction zone a room temperature knock-out pot (1 gallon) is installed to collect the condensate from the reactor effluent. After purging nitrogen, HCl and lights, reaction product samples are collected for analysis.

Following each run, the reactor tube is cleaned to remove coke deposits. For runs in which total coke production is to be quantified, the coke is collected and weighed. To assess the amount of coke suspended within a reaction product sample, all volatiles are removed via low temperature, reduced pressure distillation followed by drying the solids overnight in a vacuum oven.

The reaction product sample is lightly sparged with air to remove the bulk of any remaining M1 or HCl. Portions of the solutions, typically dark in color, are filtered (0.1 μm PTFE membrane) to remove particles of coke suspended in the sample. The filtered sample is then analyzed with an Agilent 6890 GC equipped with an automated sampling tower and thermal conductivity detector (TCD). The details of the method are given below.

| | |
|---|---|
| Column: | J&W Scientific DB-5 (Cat. 122-5032) 30 m × 0.25 mm (0.25 μm film) |
| Temperatures: | Column: 40° C. to 250° C. (2 min) at 10°/min |
| | Injector: 250° C. |
| | Detector: 275° C. |
| Flows: | Flow-1.0 ml/min (He)-constant flow |
| Split: | 100:1 |
| Detector: | TCD |

Accurate wt. % analyses are possible for the following components via multipoint calibrations with known standards: M2, M3, M4, DCE, DCP and HCA. All other reaction products, typically heavier than DCP, are assigned the same response factor as DCP since most are unavailable for calibration. $^1$H NMR spectroscopy is used to confirm the identity of the isomers of DCP working under the assumption that the trans isomers should possess a higher $J_{H-H}$ (CHCl=CH—) coupling constant than the cis. Analysis of DCP in $CH_2Cl_2$ yielded a $J_{H-H}$ of ~15 Hz for the trans isomer and a $J_{H-H}$ of ~7 Hz for the cis isomer. The cis and trans isomers of DCE are assigned within the GC method based on the known boiling points, 60° C. and 48° C. respectively.

GC/MS analysis of the crude reaction mixture identifies the cis and trans isomers of 1,3-dichloropropene as the major products, along with smaller amounts of C5, C6, and C7 compounds. Assignments for the number of DCE and M1 equivalents within each product, along with the GC retention times, are listed in Table 1, below.

TABLE 1

| Retention Time (min) | Compound[a] | DCE Equiv. in Product | M1 Equiv. in Product |
|---|---|---|---|
| 2.20 | $CH_3Cl$ (M1) | — | 1 |
| 2.51 | $CH_2Cl_2$ (M2) | — | 1 |
| 2.60 | cis-CHCl=CHCl (DCE) | 1 | — |
| 2.82 | trans-CHCl=CHCl (DCE) | 1 | — |
| 2.90 | $CHCl_3$ (M3) | — | — |
| 3.20 | $CCl_4$ (M4) | — | — |
| 3.95 | cis-CHCl=CH—$CH_2Cl$ (DCP) | 1 | 1 |
| 4.24 | trans-CHCl=CH—$CH_2Cl$ (DCP) | 1 | 1 |
| 5.38 | CHCl=CH—$CH_2$—CH=CH—$CH_2Cl$ (DCHDE) | 2 | 2 |
| 8.26 | CCl=CH—CHCl—CH=CHCl (TCPDE) | 2 | 1 |
| 8.97 | CCl=CH—CHCl—CH=CHCl (TCPDE) | 2 | 1 |
| 13.66 | $C_7H_5Cl_6$ (TCHTE) | 3 | 1 |

[a]If listed, regioisomers determined via NMR.

Upon collection of the reaction product samples, crude liquid and solid coke, conversion/selectivity assessments are available via the following calculations. Equations 1.1 and 1.2 yielded percent DCE conversion and selectivity to DCP respectively, based on GC analysis of the reaction product samples using the DCE equivalent assignments listed in Table 9.

$$Conv_{liq}^{DCE} = \frac{\Sigma(\text{mol \% DCE derived product}) * (\text{\# DCE equiv. in product})}{(\Sigma(\text{mol \% DCE derived product}) * (\text{\# DCE equiv. in product})) + \text{mol \% DCE}} \quad (1.1)$$

$$Select_{liq}^{DCE} = \frac{(\text{mol \% DCP})}{(\Sigma(\text{mol \% DCE derived product}) * (\text{\# DCE equiv. in product}))} \quad (1.2)$$

Quantization of the coke produced from selected runs enables calculation of DCE conversion to coke according to equation 1.3; a molecular weight of 24 grams per mol of DCE consumed is estimated for the coke material. Summing the results from equations 1.1 and 1.3 yields total DCE conversion (equation 1.4).

$$Conv_{coke}^{DCE} = \frac{\text{g coke produced}}{\text{g DCE fed}} * \frac{MW\ DCE}{24} \quad (1.3)$$

$$Conv_{Total}^{DCE} = Conv_{liq}^{DCE} + Conv_{coke}^{DCE} \quad (1.4)$$

The selectivity of DCE conversion to coke is then obtained via the percentage of DCE converted to coke relative to total DCE conversion (equation 1.5). Total DCE selectivity was calculated as the amount of DCE converted to DCE relative to total conversion (equation 1.6).

$$Select_{coke}^{DCE} = \frac{Conv_{coke}^{DCE}}{Conv_{Total}^{DCE}} \quad (1.5)$$

$$Select_{Total}^{DCE} = \frac{Conv_{liq}^{DCE} * Select_{liq}^{DCE}}{Conv_{Total}^{DCE}} \quad (1.6)$$

Inspection of the data listed in Table 2 reveals a high selectivity to DCP, greater than 97%, based upon analysis of the liquid phase products. As highlighted by Table 1 above, no evidence of products arising from a second addition of M1 (i.e. 1,4-dichloro-2-butene) is seen, even for runs with a high M1:DCE ratio. Rather, the principle reaction byproducts are trichloropentadiene and trichloroheptatriene.

While selectivity to DCP is quite high based on the GC analysis of the reaction product samples, the inclusion of coke formation dramatically lowers the overall DCE selectivity. For example, the liquid phase selectivity to DCP for Run 4 (Table 2) is 97.95 at 6.9% DCE conversion. However, quantitation of the coke that forms over the course of 80 g DCE fed suggests 2 mol % of DCE is converted to coke (22.9% selectivity), yielding an overall DCP selectivity of 75.5% at 9.0% DCE conversion.

TABLE 2

| | Conditions | | | Mole Fractions of Feeds | | | | | | DCE | DCP | | Analysis | | | |
| | | | | | | | | | | | | | DCEE | DCP | Trans: Cis | Cis: Trans |
| Run # | Temp (C.) | Press (sig) | GHSV (hr$^{-1}$) | X N2 | X M1 | X DCE | X HCA | X M4 | M1: DCE | Conv. (liq.)$^a$ | Select. (liq.)$^b$ | Coke Select. | Conv. (total) | Select. (total) | DCE Crude | DCP Crude |
| 1 | 420 | 260 | 1150 | — | 0.52 | 0.48 | 0.002 | — | 1.06 | 14.2% | 92.5% | — | — | — | 2.3 | 1.1 |
| 2 | 350 | 400 | 911 | — | 0.52 | 0.48 | 0.002 | — | 1.06 | 4.2% | 97.7% | — | — | — | 4.4 | 1.1 |
| 3 | 380 | 260 | 883 | — | 0.50 | 0.50 | 0.002 | — | 1.02 | 5.9% | 98.5% | — | — | — | 3.6 | 1.1 |
| 4 | 380 | 400 | 871 | — | 0.51 | 0.49 | 0.002 | — | 1.05 | 6.9% | 97.9% | 22.9% | 9.0% | 75.5% | 3.3 | 1.1 |
| 5 | 380 | 400 | 848 | — | 0.68 | 0.31 | 0.001 | — | 2.20 | 7.7% | 97.6% | — | — | — | 3.7 | 1.1 |
| 6 | 380 | 400 | 864 | — | 0.80 | 0.20 | 0.001 | — | 4.05 | 9.0% | 98.7% | 8.8% | 9.9% | 90.0% | 4.5 | 1.1 |
| 7 | 380 | 400 | 879 | 0.37 | 0.33 | 0.30 | 0.002 | — | 1.08 | 6.5% | 97.2% | 8.9% | 7.2% | 88.5% | 2.9 | 1.1 |
| 8 | 380 | 400 | 866 | — | 0.50 | 0.48 | — | 0.02 | 1.05 | 4.9% | 98.6% | — | — | — | 3.7 | 1.1 |
| 9 | 400 | 400 | 880 | — | 0.50 | 0.47 | — | 0.02 | 1.06 | 7.5% | 96.7% | — | — | — | 2.7 | 1.1 |
| 10 | 380 | 400 | 867 | — | 0.51 | 0.49 | — | — | 1.05 | 4.3% | 99.3% | — | — | — | 3.8 | 1.1 |
| 11 | 400 | 400 | 873 | — | 0.51 | 0.49 | — | — | 1.04 | 7.3% | 97.9% | — | — | — | 3.1 | 1.1 |
| | | | | | | | | | | | | | DCE from Aldrich | | 5.9 | — |
| | | | | | | | | | | | | | DCP from Aldrich | | — | 1.1 |

$^a$Based on GC analysis of crude liquid using equation 1.1.
$^b$Based on GC analysis of crude liquid using equation 1.2.

TABLE 3

| Run # | Temp (C.) | Press (psig) | GHSV (hr$^{-1}$) | X N2 | X DCP | DCP Conv. (liq.) | Select. to DCE (liq.) | Select. to TCPDE (liq.) | Select. to TCHTE (liq.) | DCP Conv. to Coke | DCP Conv. (total) | DCP Select. to Coke | Cis: Trans DCP Crude |
| 12 | 400 | 400 | 342 | 95.6 | 4.4 | 1.1% | 49.8% | 34.6% | 15.6% | 6.9% | 8.0% | 86.2% | 1.7 |

As shown in Table 2, a ~17% increase in DCE conversion is observed when the reaction pressure is raised from 260 psig (Run 3) to 400 psig (Run 4) at constant flow rate and feed composition. And, several comparative runs (Run 1/Run 3, Run 2/Run 4, Run 8/Run 9, Run 10/Run 11) demonstrate an increase in DCE conversion (liquid phase analysis) as the reaction temperature is increased.

Doubling the M1:DCE feed ratio (Run 4/Run 6) significantly reduces coke selectivity, ~9% (Run 6) relative to ~23% (Run 4), even at higher DCE conversion. While the reaction of DCP radical with M1 may be partially responsible for the increase in selectivity, the use of nitrogen (Run 7) as a diluent (37% of total feed) with the standard M1:DCE ratio of 1:1 also leads to a significant decrease in coke selectivity (~9%) compared to an undiluted run (23% coke selectivity).

As shown in Table 3, (Run 12), a 4.4 mol % feed of DCP in nitrogen, designed to simulate typical outlet concentrations during DCP production from M1 and DCE, is passed through the reactor at 400° C. and 400 psig. While analysis of the reaction product samples (~50% 12DCE, ~35% TCPDE, and ~15% TCHTE) suggests a DCP conversion of 1.1%, the coke that collects (1.3 g coke) from the run (87.8 g DCP fed) suggests a total DCP conversion of 8% with an 86% selectivity to coke.

These examples show that the production of 1,3-dichloropropene (DCP) from 1,2-dichloroethylene (DCE) and methyl chloride (M1) is a viable alternative process to the production of DCP as a by-product of allyl chloride production. More specifically, these examples show that reaction conditions including temperatures of from 390° C. to 420° C. and pressures of from 200 psig to 400 psig with <5 mole % of M4 initiator level are commercially viable. These examples further show that higher temperature, pressure, M1/DCE ratio and initiator level is beneficial to increase reactor productivity and that high selectivity (e.g., greater than 90%) can be achieved with high conversion of DCE.

The invention claimed is:

1. A one-step process for the production of chlorinated and/or fluorinated propenes comprising: reacting i) a dichloroethylene or a chlorofluoroethylene having the formula CHCl=CHX wherein X is Cl or F; and ii) a methane, chloromethane, fluoromethane or chlorofluoromethane having the formula $CH_{(4-a)}X_a$, wherein a is 0-3, to provide at least one chlorinated and/or fluorinated propene.

2. The process of claim 1, wherein the chlorinated and/or fluorinated propene has the formula CHX=CH—$CH_{(3-a)}X_a$ wherein a is 0-3.

3. The process of claim 1, wherein the process carried out at a temperature of less than 600° C.

4. The process of claim 3, wherein the process is carried out at a temperature of less than 500° C.

5. The process of claim 1, wherein the process is carried out at ambient pressure or greater.

6. The process of claim 5, wherein the process is carried out at a pressure of greater than 200 psig.

7. The process of claim 1, wherein the reaction is carried out in the presence of one or more catalyst(s) and/or initiator(s).

8. The process of claim 7, wherein the initiator comprises carbon tetrachloride, chlorine, hexachloroethane, benzotrichloride, hexachloroacetone or combinations of these.

9. The process of claim 1, wherein the methane, chloromethane, fluoromethane or chlorofluoromethane and the chloroethylene or chlorofluoroethylene are provided in a ratio of $CH_{(4-a)}X_a$/CHCl=CHX of greater than or equal to 1.0.

10. The process of claim 9, wherein the reactor further makes use of a diluent to reduce the temperature within the reactor, wherein the diluent comprises an inert diluent, $CH_{(4-a)}X_a$, HCl, or combinations of these.

11. The process of claim 1, wherein the chlorinated and/or fluorinated propene comprises cis/trans 1,3-dichloropropene.

12. The process of claim 11, wherein the dichloroethylene or chlorofluoroethylene comprises cis/trans 1,2-dichloroethylene and the methane, chloromethane, fluoromethane or chlorofluoromethane comprises methyl chloride.

13. The process of claim 12; wherein the methyl chloride and/or 1,2-dichloroethylene are generated for use in the process.

14. The process of claim 4, wherein the pressure is greater than 15 psia and the process is carried out in the presence of a catalyst/initiator, and the molar ratio of $CH_{(4-a)}X_a$/CHCl=CHX is greater than 1.0.

15. The process of claim 1, wherein the CHCl=CHX and/or $CH_{(4-a)}X_a$ are recycled within the process.

16. The process of claim 15, where byproducts with boiling points in between $CH_{(4-a)}X_a$, and CHCl=CHX are removed from the process by purging or distillation prior to recycling of $CH_{(4-a)}X_a$ and CHCl=CHX.

17. A one-step process for the production of chlorinated propenes comprising: reacting i) a dichloroethylene having the formula CHCl=CHCl; and ii) a methane or chloromethane having the formula $CH_{(4-a)}Cl_a$, wherein a is 0-3, to provide at least one chlorinated propene.

18. The process of claim 17, wherein the chlorinated propene has the formula CHCl=CH—$CH_{(3-a)}Cl_a$ wherein a is 0-3.

19. The process of claim 17, wherein the process carried out at a temperature of less than 600° C.

20. The process of claim 17, wherein the process is carried out at a pressure of greater than 200 psig.

21. The process of claim 17, wherein the reaction is carried out in the presence of one or more catalyst(s) and/or initiator(s).

22. A one-step process for the production of 1,3-dichloropropenes comprising reacting 1,2-dichloroethylene and methyl chloride at a ratio of at least 1:1, a temperature of less than 600° C., and ambient pressure or higher to provide a mixture of 1,3-dichloropropenes.

* * * * *